(12) United States Patent
Butruille et al.

(10) Patent No.: US 11,990,205 B2
(45) Date of Patent: May 21, 2024

(54) SYSTEMS AND METHODS FOR USE IN IDENTIFYING MULTIPLE GENOME EDITS AND PREDICTING THE AGGREGATE EFFECTS OF THE IDENTIFIED GENOME EDITS

(71) Applicant: Monsanto Technology LLC, St. Louis, MO (US)

(72) Inventors: David Vincent Butruille, Des Moines, IA (US); Lex Evan Flagel, Arden Hills, MN (US)

(73) Assignee: Monsanto Technology LLC, Saint Louis, MO (US)

( * ) Notice: Subject to any disclaimer, the term of this patent is extended or adjusted under 35 U.S.C. 154(b) by 1757 days.

(21) Appl. No.: 15/940,695

(22) Filed: Mar. 29, 2018

(65) Prior Publication Data
US 2018/0285520 A1  Oct. 4, 2018

Related U.S. Application Data

(60) Provisional application No. 62/479,032, filed on Mar. 30, 2017.

(51) Int. Cl.
*G16B 20/00* (2019.01)
*A01H 1/04* (2006.01)
(Continued)

(52) U.S. Cl.
CPC ............... *G16B 20/00* (2019.02); *A01H 1/04* (2013.01); *C12N 15/8261* (2013.01);
(Continued)

(58) Field of Classification Search
CPC .......... A01H 1/04; G16B 40/00; G16B 20/50; G16B 20/00; C12N 15/8261; C12Q 1/6895
(Continued)

(56) References Cited

U.S. PATENT DOCUMENTS 8,697,359 B1   4/2014 Zhang
2005/0188434 A1  8/2005 Spencer et al.
(Continued)

FOREIGN PATENT DOCUMENTS

CA    2946881    11/2015
CN   102369531    3/2012
(Continued)

OTHER PUBLICATIONS

Anne-Michelle Faux, Gregor Gorjanc, R. Chris Gaynor, Mara Battagin, Stefan M. Edwards, David L. Wilson, Sarah J. Hearne, Serap Gonen, John M. Hickey: AlphaSim: Software for Breeding Program Simulation, The Plant Genome, vol. 9 Issue 3, Nov. 1, 2016 (Year: 2016).*

(Continued)

*Primary Examiner* — Russell S Negin
*Assistant Examiner* — Guozhen Liu
(74) *Attorney, Agent, or Firm* — Harness, Dickey & Pierce, P.L.C.

(57) ABSTRACT

Exemplary systems and methods for selecting from population of candidate edits and predicting an aggregate effect of the candidate edits are disclosed. One exemplary method includes identifying a population of candidate edits to a genomic sequence of said organism and ranking each of the candidate edits based on a predicted ability of each candidate edit to affect a trait of interest in said organism. The exemplary method further includes selecting one or more of the candidate edits based on the ranking and predicting, by the computing device, an aggregate effect of the selected one or more of the candidate edits for the trait of interest when expressed by a specimen of the organism having a genomic sequence and edited according to the selected one or more of the candidate edits, as compared to an unedited specimen of the organism.

10 Claims, 3 Drawing Sheets

(51) Int. Cl.
  *C12N 15/82* (2006.01)
  *C12Q 1/6895* (2018.01)
  *G16B 20/50* (2019.01)
  *G16B 40/00* (2019.01)
  *G16B 20/20* (2019.01)
  *G16B 25/00* (2019.01)

(52) U.S. Cl.
  CPC ........... *C12Q 1/6895* (2013.01); *G16B 20/50* (2019.02); *G16B 40/00* (2019.02); *C12N 15/8243* (2013.01); *Y02A 40/146* (2018.01)

(58) Field of Classification Search
  USPC .......................................................... 702/20
  See application file for complete search history.

(56) References Cited

U.S. PATENT DOCUMENTS

| | | |
|---|---|---|
| 2010/0037342 A1 | 2/2010 | Johnson et al. |
| 2012/0060233 A1 | 3/2012 | Kennard et al. |
| 2013/0005590 A1 | 1/2013 | Lou et al. |
| 2014/0283213 A1 | 9/2014 | Buyyarapu et al. |
| 2015/0019190 A1 | 1/2015 | Danter |
| 2015/0181822 A1 | 7/2015 | Daetwyler et al. |
| 2016/0029604 A1 | 2/2016 | Fahrenkrug et al. |
| 2016/0292355 A1 | 10/2016 | Lou et al. |
| 2022/0361428 A1 | 11/2022 | Butruille et al. |

FOREIGN PATENT DOCUMENTS

| | | |
|---|---|---|
| CN | 103189550 A | 7/2013 |
| WO | WO-2014/015196 A2 | 1/2014 |
| WO | WO2015/103430 | 7/2015 |

OTHER PUBLICATIONS

Martha T. Hamblin, Edward S. Buckler, Jean-Luc Jannink: ("Population genetics of genomics-based crop improvement methods", Trends in Genetics, vol. 27, Issue 3, Mar. 2011, pp. 98-106 (Year: 2011).*

Belhaj, Khaoula, et al. "Plant genome editing made easy: targeted mutagenesis in model and crop plants using the CRISPR/Cas system." Plant methods 9.1 (2013): 1-10. (Year: 2013).*

Naqvi, Shaista, et al. "When more is better: multigene engineering in plants." Trends in plant science 15.1 (2010): 48-56. (Year: 2010).*

Jenko, J., G. Gorjanc, M.A. Cleveland, R.K. Varshney, C.B. A. Whitelaw, J.A. Woolliams, and J.M. Hickey. (2015) Erratum to: Potential of promotion of alleles by genome editing to improve quantitative traits in livestock breeding programs. Genetics Selection Evolution 47:69, 3 pages. DOI: 10.1186/s12711-015-0144-2.

Jenko, J., G. Gorjanc, M.A. Cleveland, R.K. Varshney, C.B. A. Whitelaw, J.A. Woolliams, and J.M. Hickey. (2015) Potential of promotion of alleles by genome editing to improve quantitative traits in livestock breeding programs. Genetics Selection Evolution 47:55, 14 pages. DOI: 10.1186/s12711-015-0135-3.

Pearson, This Startup Says AI Can Predict the Effects of Gene Editing, In: motherboard.vice.com, Jul. 22, 2015 (Jul. 22, 201) [online] [retrieved on Jul. 16, 2018 (Jul. 16, 2018)] Retrieved from the Internet<URL: https://motherboard.vice.com/en_us/article/4x394p/this-startup-says-ai-can-predict-the-effects-of-gene-editing>, 4 pages.

Frisch & Melchinger (2005) *Genetics* 170(2):909-917, Selection Theory for Marker-Assisted Backcrossing.

Jens Nielsen et al: Chapter 3, "Analysis of Reaction Rates", Jan. 1, 1994, Bioreaction Engineering Principles, Plenum Press, US, pp. 97-161.

Dersch, Lisa Maria et al: "Green pathways: 1-5 Metabolic network analysis of plant symbols", Metabolic Engineering, Academic Press, US, vol. 34, Dec. 17, 2015, pp. 1-24.

Yingjie Xiao et al: "Genome-wide Association Studies in Maize: Praise and Stargaze", Molecular Plant, vol. 10, No. 3, Mar. 6, 2017, pp. 359-374.

Nogué, Fabien, et al. "Genome engineering and plant breeding: impact on trait discovery and development." Plant cell reports 35 (2016): 1475-1486. 12 pages.

* cited by examiner

SYSTEMS AND METHODS FOR USE IN IDENTIFYING MULTIPLE GENOME EDITS AND PREDICTING THE AGGREGATE EFFECTS OF THE IDENTIFIED GENOME EDITS

CROSS-REFERENCE TO RELATED APPLICATION

This application claims the benefit of and priority to U.S. Provisional Application No. 62/479,032, filed on Mar. 30, 2017. The entire disclosure of the above application is incorporated herein by reference.

FIELD

The present disclosure generally relates to systems and methods for use in statistical genome editing, and in particular, to systems and methods for use in identifying potential genome edits, rating the potential edits based on one or more parameters, and predicting an aggregate effect of multiple rated genome edits on one or more given traits.

BACKGROUND

This section provides background information related to the present disclosure which is not necessarily prior art.

Plants, animals, and other organisms are bred and raised for commercial and scientific purposes. Conventional breeding techniques for improving plant and animal stocks rely on controlled matings or crosses of parents, in which each parent conveys a given allele to produce at least one progeny organism comprising all relevant alleles in a single genome. Among organisms with diploid or polyploid genomes, the production of a true-breeding stock with the requisite combination of alleles requires not merely that all of the alleles be found in the single genome, but that the allele for each locus in question be found on both or all chromosome sets (for diploid and polyploid organisms, respectively). This may require many hundreds, thousands, or more crosses, depending on the number of traits that need to be introgressed into a given stock, which can be very time consuming and taxing on cultivation and husbandry resources.

Deliberate and directable genome editing technologies—in particular the clustered regularly interspersed short palindromic repeats (CRISPR) technology (see, e.g., U.S. Pat. No. 8,697,359)—are known to accelerate the process of introducing traits into a germ line to reduce the number of cross-matings that are necessary to generate a stable line with the desired traits. When CRISPR is paired with a Cas nuclease—particularly Cas9—CRISPR can effectuate very precise and efficient editing of nucleotide sequences. Instead of relying on the random chance of a meiotic crossover to bring a given set of loci together onto a single chromosome, CRISPR and related genome editing technologies, such as zinc-finger nucleases (ZFNs) and transcription activator-like effector nucleases (TALENs), make it possible for an artisan to manipulate chromosomes in a deliberate, directed manner to assemble alleles together. Moreover, Jenko et al., (2015) *Genetics Selection Evolution* 47:55, report that promotion of alleles by genome editing (PAGE) can accelerate the rate at which multiple traits can be integrated into a true-breeding germ line.

DRAWINGS

The drawings described herein are only for illustrative purposes of selected embodiments and are not intended to limit the scope of the present disclosure.

Corresponding reference numerals indicate corresponding parts throughout the several views of the drawings.

DETAILED DESCRIPTION

Exemplary embodiments will now be described more fully with reference to the accompanying drawings. The description and specific examples included herein are intended for purposes of illustration only and are not intended to limit the scope of the present disclosure.

Plants, animals and other organisms are bred and/or modified to fulfill commercial or scientific purposes. Genome editing techniques aim to accelerate the process of introducing traits into genomes. A universe of potential genome edits for a given organism, however, is substantial, with each edit potentially having a different effect on one or more traits of interest, in both direction and magnitude. And further, a given genome edit may have positive or negative effects on the traits of interest. It is understood herein that challenges related to confirming genome edits exist as the effects may fall below one or more thresholds of detection in experiments of a certain size. Uniquely, the systems and methods herein provide for the selection of multiple candidate edits and prediction of the aggregate effect of the multiple edits, whereby separate and/or individual testing of single edits, may be omitted and/or avoided. In particular, a population of candidate edits for a genome sequence related to one or more traits of interest is identified, from which multiple candidate edits (e.g., edits at multiple genome locations, etc.) are selected, by a genome editing engine, based on a ranking of the candidate edits. An aggregate effect of the multiple selected candidate edits is then predicted, again, by the genome editing engine, for a trait of interest when expressed by an organism having a genomic sequence edited according to the selected candidate edits (as compared to an organism having the same genomic sequence, but unedited). Once the aggregate effect is predicted, the selected genome edits may be subject to validation, for example, via a genome editing scheme, whereby the genome of an organism is modified to include the multiple selected candidate edits and tested for purposes of verification of the aggregate effect on the one or more traits of interest (and not the impact of the edits individually). Size and/or arrangement of samples of the organism are selected, as described herein, to limit the sample size, while providing sufficient confidence in the multiple edits in the genome sequence and their effect on the one or more traits of interest of the organism.

Figure 1:
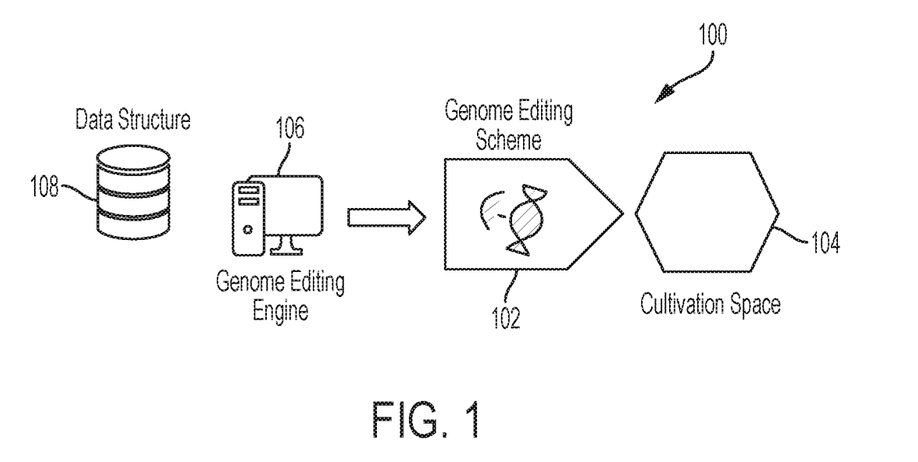
FIG. 1 is a block diagram of an exemplary system of the present disclosure suitable for use in subjecting genomes to potential genome editing based on ratings associated with the genome editing.

FIG. 1 illustrates an exemplary system 100 in which the one or more aspects of the present disclosure may be implemented. Although the system 100 is presented in one arrangement, other embodiments may include the parts of the system 100 (or additional parts) arranged or otherwise depending on, for example, the manner in which the multiple genome edits are identified, selected, and/or edited into a genome sequence of an organism, etc.

In the exemplary embodiment of FIG. 1, the system 100 generally includes a genome editing scheme 102 and a cultivation space 104, in which one or more plants, animals, bacteria, fungi, viruses, or other organisms, produced from the genome editing scheme 102, are bred, grown, matured, and/or cultured, etc. The genome editing scheme 102 is provided as an environment in which potential genome edits (as determined herein) are executed in connection with target organisms.

In the genome editing scheme 102, the genome edits are generally made, for example, in gamete cells (however, this is not required in all embodiments). In certain embodiments, for example, the genome edits are made in a zygote, and are effectuated in target cells in a multicellular potential parent organism—for example a sexually mature parent organism—using a vector such as, for example, a viral vector with specific tropism for particular tissues (e.g., gametogenic tissues, etc.). The molecular biologist of ordinary skill is familiar with such techniques, and knows when to use one in preference to another to effectuate a given manipulation in the target organism's genome. Additionally, these manipulations may be achieved with one or more of: CRISPR technology, and particularly with CRISPR/Cas technology and more particularly CRISPR/Cas9 technology; ZFNs; TALENs; homologous recombination; etc. With that said, the above is provided without limitation. The appropriate technique will be identified and executed by the ordinarily skilled artisan in accordance with the type and/or degree of manipulation of the organism selected and/or required.

Regardless of the precise technique(s) used to effectuate the candidate edits in a target organism's genome sequence in the genome editing scheme 102, the artisan can use one or more of the modified potential parent organisms in a paired cross to introduce a desired trait or traits into their progeny. In connection therewith in the illustrated embodiment, the breeding of the potential parent organisms to introgress the desired trait or traits into the target organism's germ line may be performed in the cultivation space 104. Techniques for arranging and assessing paired crosses necessary to produce true-breeding germ lines in a target organism are known in the art (See, e.g., Frisch & Melchinger (2005) *Genetics* 170(2):909-17, etc.).

In one example, where the parent organisms are plants, the cultivation space 104 may be any suitable area for cultivation of plants, and may include, for example, pots, trays, grow rooms, greenhouses, plots, gardens, fields, combinations thereof, or the like. In addition, in certain embodiments, the plants may be cultured hydroponically in suitable aqueous media. In any case, the size and/or configuration of the cultivation space 104 may be determined by those of ordinary skill in the art, and will often vary according to the number and/or type of plants involved. Alternatively, where the parent organisms are mammals, such as cows, horses, pigs, etc., the cultivation space 104 may be any suitable area for animal husbandry and may include, for example, such as cages, pens, kennels, stables, barns, feed-lots, combinations thereof, or the like. Where the parent organisms are birds, such as chickens, turkeys, or ducks, the cultivation space 104 may be any suitable area for bird farming and/or breeding, and may include, for example, pens, cages, aviaries, henhouses, roosts, ponds, combinations thereof, or the like. And, where the parent organisms are fish, such as salmon, trout, or zebrafish, the cultivation space 104 may be any suitable area for aquaculture, and include, for example, tanks, tubs, ponds, combinations thereof, or the like. The size and/or configuration of the cultivation space 104 will vary according to the number and/or type of animals involved, and choices about size and/or configuration of the cultivation space 104 will be familiar to those of ordinary skill in the appropriate art (e.g., husbandry, aquaculture, etc.).

Alternatively, where the parent organisms are bacteria, fungi, or viruses, such as *Escherichia coli, Lactococcus, Lactobacillus, Streptococcus, Aspergillus, Saccaromcyes*, Tobacco mosaic tobamovirus, Human immunodeficiency virus, Influenza A virus, or T4 phage, etc., the cultivation space 104 may be any suitable space for microbial culture and may include, for example, petri dishes, flasks, agar plates, incubators, coolers, combinations thereof, or the like. The instruments may be sterilized with an autoclave or equivalent. The size and/or configuration of the cultivation space 104 may vary according to the number and/or type of bacteria or fungi involved. Consistent with the above, the size and/or configuration of the cultivation space 104 may be determined by those of ordinary skill in the appropriate art (e.g., microbial culturing, etc.).

Figure 2:
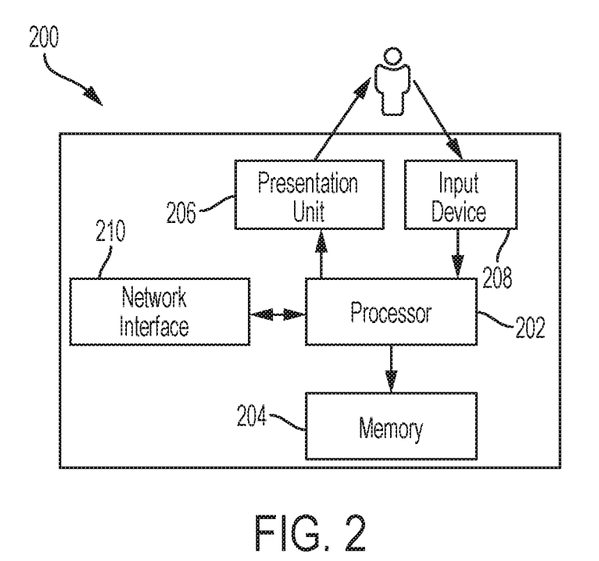
FIG. 2 is a block diagram of a computing device that may be used in the exemplary system of FIG. 1.

FIG. 2 illustrates an exemplary computing device 200 that can be used in the system 100. The computing device 200 may include, for example, one or more servers, workstations, personal computers, laptops, tablets, smartphones, etc. In addition, the computing device 200 may include a single computing device, or it may include multiple computing devices located in close proximity or distributed over a geographic region, so long as the computing devices are specifically configured to operate as described herein. In the exemplary embodiment of FIG. 1, each of the genome editing scheme 102 and the cultivation space 104 may include one or more computing devices consistent with computing device 200. Also, in the exemplary embodiment, the system 100 includes a genome editing engine 106 (described in more detail below) and a data structure 108, each of which may be understood to be consistent with the computing device 200 and/or implemented in a computing device consistent with computing device 200 (or a part thereof, such as, for example, memory 204, etc.). However, the system 100 should not be considered to be limited to the computing device 200, as described below, as different computing devices and/or arrangements of computing devices may be used. In addition, different components and/or arrangements of components may be used in other computing devices.

As shown in FIG. 2, the exemplary computing device 200 includes a processor 202 and a memory 204 coupled to (and in communication with) the processor 202. The processor 202 may include one or more processing units (e.g., in a multi-core configuration, etc.). For example, the processor 202 may include, without limitation, a central processing unit (CPU), a microcontroller, a reduced instruction set computer (RISC) processor, a graphics processing unit (GPU), an application specific integrated circuit (ASIC), a programmable logic device (PLD), a gate array, and/or any other circuit or processor capable of the functions described herein.

The memory 204, as described herein, is one or more devices that permit data, instructions, etc., to be stored therein and retrieved therefrom. In connection therewith, the memory 204 may include one or more computer-readable storage media, such as, without limitation, dynamic random access memory (DRAM), static random access memory (SRAM), read only memory (ROM), erasable programmable read only memory (EPROM), solid state devices, flash drives, CD-ROMs, thumb drives, floppy disks, tapes, hard disks, and/or any other type of volatile or nonvolatile physical or tangible computer-readable media for storing such data, instructions, etc. In particular herein, the memory 204 is configured to store data including, without limitation, genome sequences, phenotypic data for traits of interest, haplotype characterization, genome annotations, DNA sequences, exome sequences, comparative sequences, peptide and protein sequences, candidate edits, genome-wide association study (GWAS) analyses, probabilities of effects of genome edits, magnitudes of such effects, non-parametric classification parameters, gene expression data, biochemical pathway model(s), and/or other types of data (and/or data structures) suitable for use as described herein. Furthermore, in various embodiments, computer-executable instructions may be stored in the memory 204 for execution by the processor 202 to cause the processor 202 to perform one or more of the operations described herein in connection with the various different parts of the system 100, such that the memory 204 is a physical, tangible, and non-transitory computer readable storage media. Such instructions often improve the efficiencies and/or performance of the processor 202 that is performing one or more of the various operations herein. It should be appreciated that the memory 204 may include a variety of different memories, each implemented in connection with one or more of the functions or processes described herein.

In the exemplary embodiment, the computing device 200 also includes a presentation unit 206 that is coupled to (and is in communication with) the processor 202 (however, it should be appreciated that the computing device 200 could include output devices other than the presentation unit 206, etc.). The presentation unit 206 may output information (e.g., candidate edits, traits of interest, predicted aggregate effects of genome edits, etc.), visually to a user of the computing device 200, such as a breeder or other person associated with selection of a nature of edits, etc. It should be further appreciated that various interfaces (e.g., as defined by network-based applications, websites, etc.) may be displayed at computing device 200, and in particular at presentation unit 206, to display certain information to the user. The presentation unit 206 may include, without limitation, a liquid crystal display (LCD), a light-emitting diode (LED) display, an organic LED (OLED) display, an "electronic ink" display, speakers, etc. In some embodiments, presentation unit 206 may include multiple devices. Additionally or alternatively, the presentation unit 206 may include printing capability, enabling the computing device 200 to print text, images, and the like on paper and/or other similar media.

In addition, the computing device 200 includes an input device 208 that receives inputs from the user (i.e., user inputs) such as, for example, selections of gene sequences and/or one or multiple candidate edits of genomes, passing of selected candidate edits for validation, measuring of sample organisms during validation, etc. The input device 208 may include a single input device or multiple input devices. The input device 208 is coupled to (and is in communication with) the processor 202 and may include, for example, one or more of a keyboard, a pointing device, a mouse, a stylus, a touch sensitive panel (e.g., a touch pad or a touch screen, etc.), or other suitable user input devices. In addition, the input device 208 may include, without limitation, sensors disposed and/or associated with the genome editing scheme 102 and/or the cultivation space 104, such as, for example, moisture probes, weight scales, near infrared spectrometers, cameras, pH-meters, and temperature sensors. It should be appreciated that in at least one embodiment an input device 208 may be integrated and/or included with an output device 206 (e.g., a touchscreen display, etc.).

Further, the illustrated computing device 200 also includes a network interface 210 coupled to (and in communication with) the processor 202 and the memory 204. The network interface 210 may include, without limitation, a wired network adapter, a wireless network adapter, a mobile network adapter, or other device capable of communicating to one or more different networks (e.g., one or more of a local area network (LAN), a wide area network (WAN) (e.g., the Internet, etc.), a mobile network, a virtual network, and/or another suitable public and/or private network capable of supporting wired and/or wireless communication among two or more of the parts illustrated in FIG. 1, etc.), including with other computing device used as described herein.

Referring again to FIG. 1, the system 100 includes the genome editing engine 106, and the data structure 108 coupled in communication thereto. The genome editing engine 106 is specifically configured by computer executable instructions to perform one or more of the operations described herein. In the illustrated embodiment, the genome editing engine 106 is shown as a standalone part of the system 100. However, in various other embodiments, it should be appreciated that the genome editing engine 106 may be associated with, or incorporated with, still other parts of the system 100, for example, the genome editing scheme 104, etc. In various embodiments, the genome editing engine 106 may be embodied in at least one computing device and accessible as a network service, via, for example, an application programming interface (API), or otherwise, etc.

In addition in the illustrated embodiment, the data structure 108 is shown as a standalone part of the system 100. However, the data structure 108 may be incorporated in the genome editing engine 106, in whole or in part, in other system embodiments, or in other parts of the system 100 shown in FIG. 1 or otherwise. Similar to the above, in various embodiments, the data structure 108 may be hosted, in whole, or in part, in the network-based memory and/or a dedicated computing device (e.g., stored locally, or remotely from the genome editing engine 106), whereby it is accessible to the genome editing engine 106 and/or users associated therewith via one or more networks.

In this exemplary embodiment, the data structure 108 includes various data, which may be used as described herein. In particular, for example, the data structure 108 may include sets of sequences, alleles, or single nucleotide polymorphisms (SNPs) that correlate, individually and/or in the aggregate, with particular phenotypic traits. For example, the data structure 108 may include a spreadsheet, a table, or a database, etc. that includes information about potential parent organisms. Such information may include both genotypic information and phenotypic information of the target organism and, in certain embodiments, both genotypic and phenotypic information for each potential parent organism. When included, the genotypic information may include whole or partial genome sequences, SNP data, etc.

Additionally, the data structure 108 may include sequence tables, SNP tables annotated to include information about known phenotypic correlations to particular sequences, or one or more sets of SNPs. Further, the set of SNPs may include at least three, for example at least six, at least 24, at least 100, at least 150, at least 200, at least 250, at least 300, at least 350, at least 400, or at least 500, etc., SNPs from a given potential parent organism. And, the sets of sequences may include at least ten Mbp, at least 50 Mbp, at least 100 Mbp, at least 500 Mbp, at least 750 Mbp, at least one Gbp, at least two Gbp, or at least 2.5 Gbp, etc., of a sequence from a given potential parent organism. The data structure 108 may further include relationships between sets of SNPs and/or sequences in the aggregate and phenotypic traits that inhere in the corresponding potential parent organisms from which the SNPs and/or sequences are derived.

In various embodiments, the data structure 108 may be based, at least in part, on the type of organism for which the system 100 will be used. That is to say, the data structure 108 may generally include, for example, without limitation, grain yield, fiber quality and yield, lint and fiber yield, sugar content, time to maturity, flowering time, plant height, stress tolerance, and/or susceptibility to lodging, etc. when the system 100 is directed to plant organisms. The data structure 108 may alternatively include, for example, without limitation, meat or fat content, growth rate, feed conversion efficiency, milk yield, egg production, and/or twinning frequency, etc. when the system 100 is directed to animal organisms. And, when the system 100 is directed to microbes, for example, the data structure 108 may include, for example, without limitation, doubling time, fermentation efficiency, protein or peptide production, drug resistance, environmental stress tolerance, infectivity, avidity, and biofilm formation, etc.

Prior to use of the genome editing engine 106, one or more persons associated with the system 100 may define a nature of edits (e.g., define desired changes in a base pair sequence, insertions, deletions, duplication, etc.), which are a target of the use of the system 100. For example, the one or more persons may define one or more output traits (e.g., a series, etc.) for an organism, such as a maize specimen. Exemplary desired traits specific to maize may include, without limitation, but more typically, traits of economic importance (which may include, for example, generally, traits (of plant, more generally) that if modified, result in an economic benefit that is of value greater than the cost required to achieve the modification, and/or that result in a benefit linked to economics or are based on economics related to developing and/or commercializing the result, etc. Traits of economic importance includes, but are not limited to, traits conferring a preferred phenotype selected from the group consisting of herbicide tolerance, disease resistance, insect or pest resistance, altered fatty acid, protein or carbohydrate metabolism, grain yield, oil content, nutritional content, growth rate, stress tolerance, preferred maturity, organoleptic properties, altered morphological characteristics, other agronomic traits, traits for industrial uses, or traits for improved consumer appeal, etc. In connection therewith, or independent from the nature of the potential edits, the one or more persons may, and/or the genome editing engine 106 is configured to, identify a genome sequence for the genome (e.g., a genome and/or a pan genome, etc.) as a starting or reference point for the processes herein. The genome editing engine 106 may do so through application of proven models for new genomes (e.g., a particular new inbred line, etc.) and/or inferences through different models (which may be proven out by experiments) and/or learning models, etc.

Further, the genome editing engine 106 may be configured to identify a population of candidate edits for the genome sequence based on one or more of, for example, genome annotation, genome-wide association study (GWAS) analysis, quantitative trait loci (QTL), gene expression data, biochemical pathway models, etc., each retrieved from the data structure 108 (and, potentially, input from one or more breeder persons). The potential edits may be selected by the ordinarily skilled artisan or by an algorithm which has identified potentially useful genetic mutations to achieve the desired phenotype. As used herein, candidate edits may include a single change in the genome or a number of simultaneous changes to a gene, set of genes, or genome. Several approaches singly or in combination will be used to select a population of candidate edits. One may use prior or newly acquired knowledge of genes and pathways known to affect the one or more traits of interest. This knowledge may have been generated through classical mutation screens, complementation tests, and/or comparisons of genomic sequences across a large number of genetically distinct individuals with varied phenotypes for the trait (as in GWAS and other types of QTL studies). Expression studies can aid by providing information about differences in transcript and protein levels among individuals with different phenotypes.

The genome editing engine 106 is configured to then rate the candidate genome edits based on a predicted ability of the candidate genome edits to affect a trait(s) of interest (e.g., phenotype or multiple phenotypes of target organism). The genome editing engine 106 may be configured to rate the candidate edits based on a probability of causing an effect, a magnitude of a predicted effect, a non-parametric classification parameter, or combinations thereof. As an example, for a user herein, the genome editing engine 106 may provide the probability that a maize plant with a particular edit will have an increased grain yield and/or degree of increased grain yield change compared to an unedited maize plant, and then rate the edits made thereon.

Then, once the candidate genome edits are rated, the genome editing engine 106 is configured to then select multiple of the candidate edits, based on the ratings, such that the selected candidate edits provide a specific and/or desired likelihood of an aggregate effect on the trait(s) of interest (e.g., as defined by the nature of the edits, etc.) (i.e., for a specimen carrying the genome and/or a population of specimen carrying the pan-genome, etc.). The genome editing engine 106 is configured to predict an aggregate effect of the selected candidate edits when expressed in the specimen on at least one of the traits of interest (e.g., yield in maize, etc.) as compared to a specimen with an unedited genomic sequence.

Thereafter, when the predicted aggregate effect is above a defined threshold, the selected candidate edits may be passed, by the genome editing engine 106 or one or more persons, to the genome editing scheme 102, whereupon specimen(s) (as defined by the genome sequence generated above) is edited consistent with the selected candidate edits. The edited specimens(s) may then be provided to the cultivation space 104, for growing and testing to confirm the predicted aggregate effect.

Figure 3:
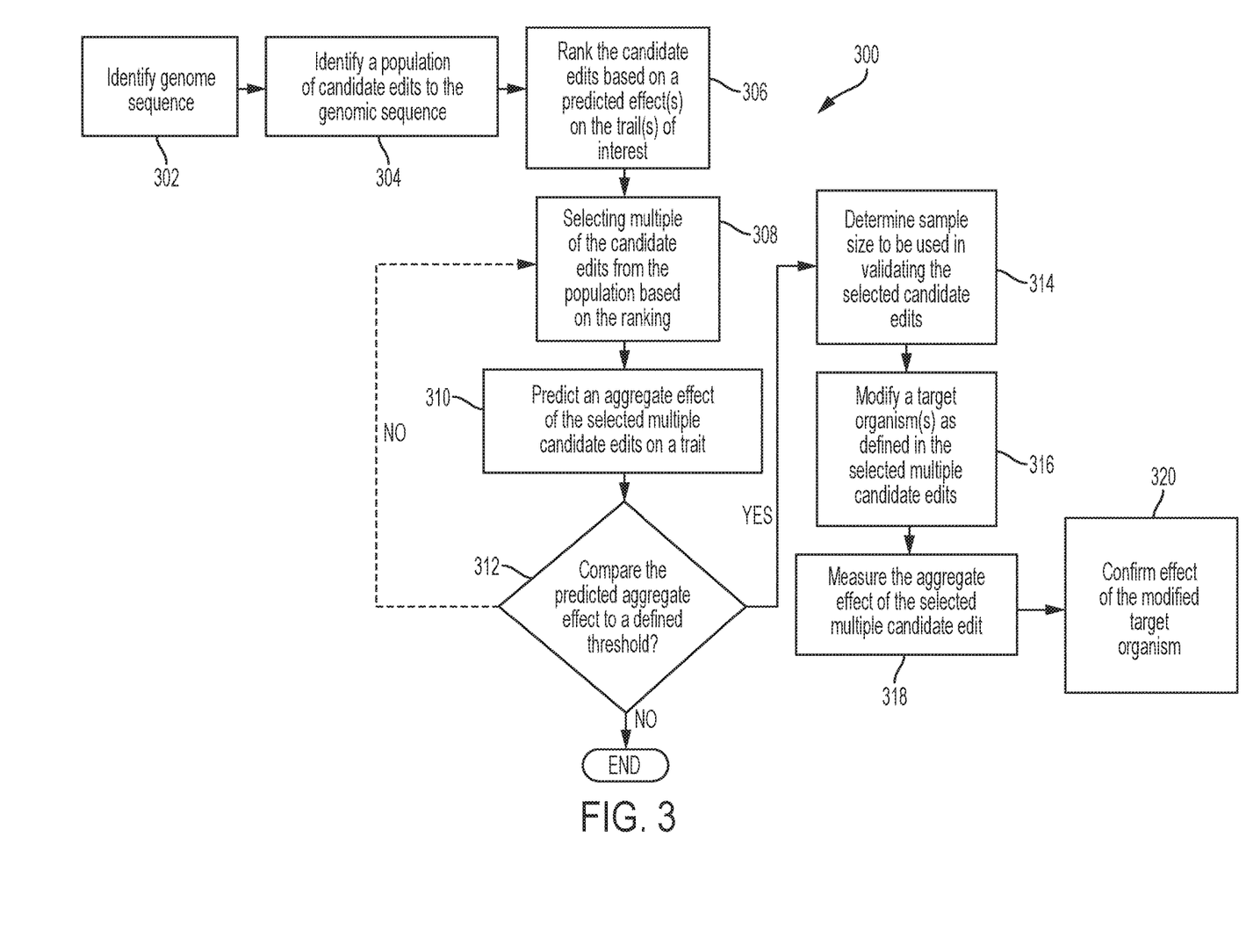
FIG. 3 is an exemplary method, suitable for use with the system of FIG. 1, for identifying potential genome edits and rating the potential genome edits for use in modifying a target organism.

FIG. 3 illustrates an exemplary method 300 for use in selecting multiple potential genome edits based on a predicted aggregate effect, for use in modifying a target organism. The exemplary method 300 is described herein in connection with the genome editing engine 106 of the system 100, and is also described with reference to computing device 200. However, it should be appreciated that the methods herein are not limited to the system 100, or computing device 200. And, likewise, the systems and computing devices described herein are not limited to the exemplary method 300. Generally, and prior to the method 300, one or more person(s) and/or entities are provided, which are tasked with defining a trait or phenotype in a type of organism to be affected. To illustrate the method 300, it is assumed that the target organism is a maize plant (e.g., inbred lines, hybrid varieties, etc.) and the nature of the candidate edits to the maize plant is to alter its grain yield. While the method 300 is described in the following with reference to the maize plant and to certain edits, it should be understood that the method 300 and the description herein is not limited to this particular example, and may be applied to other desired plants and traits in plants and to other organisms, etc.

With that said, the method 300 initially includes identifying a genome sequence of the maize plant, at 302, to which the candidate edits may or may not be made. Genome sequence identification may include, for example, de novo generation or imputation from related and/or ancestral organisms. De novo genome sequencing may be accomplished by technologies and algorithms known to those skilled in the art. Sequence information can be identified and/or generated by those skilled in the art through performing conventional methods, by third parties, or be identified from one or more resources available in the public domain.

Once the genome sequence is generated or identified at 302, the genome editing engine 106 (alone, or in combination with one or more persons) identifies, at 304, a population of candidate edits to the genomic sequence. The population of candidate edits, or available edits, is identified generally based on the nature of the traits defined at the outset. That is, in the above illustrative example related to the maize plant, the nature of the trait to be modified is related to an enhancement in the grain yield of inbred maize. Following the dominance hypothesis for hybrid vigor, for example, when editing the genomic sequence of a maize inbred line, the potential edits may be first focused on identifying genes containing stop codons within the genomic sequence that are likely to prevent proper expression of a gene associated with grain yield (i.e., "premature" stop codons). Expression studies which analyze and quantify the presence of such transcripts in hybrid maize varieties could focus the population of edits. For example, two separate maize varieties with enhanced grain yield and differential expression of distinct genes or alleles may provide insight, guidance, and/or instruction into which candidate edits should be identified for the enhanced grain yield for the inbred maize.

In one specific example of method 300, for a genome sequence for maize inbred line of the Stiff Stalk heterotic group, 481 premature stop codons were identified, each of which is predicted to truncate the protein product encoded by the gene. In connection therewith, a training data set is constructed and consists of other yield estimates from maize inbred lines that were polymorphic for the premature stop codons (i.e. shared the premature stop codon, or encoded a full-length copy of the gene). Using a statistical model, which is built based on the training data, the hybrid grain yield impact or effect of each of the 481 premature stop codons may be determined (e.g., at step 304, etc.).

It should be appreciated that in other embodiments, the genome editing engine 106 may be omitted from identifying the population of candidate edits, whereby one or more persons skilled in the art rely on information, such as that described above, to identify the candidate edits for modulating the genome sequence as it pertains to the trait of interest.

Next, the genome editing engine 106 ranks the candidate edits from the population of potential edits, at 306, based on a predicted effect(s) to the trait(s) of interest. For example, the ranking may be in an increasing or decreasing order of the predicted effect.

The ranking of edits may be, for example, based on the product (e.g., by multiplication, etc.) of the perceived probability of the edits having an effect(s) on the trait(s) of interest and the magnitude of the predicted effect(s). For example, assume that prior experience with the reversion of premature stop codons within a genome sequence restores gene function 60% of the time and that the candidate gene to be edited pertains to a gene family that displays, on average, a 0.2 bushel per acre (Bu/A) yield increase by the functional alleles as compared to the non-functional alleles. Then, the frequency-adjusted value of reverting to functional a non-functional allele at that locus would be of 0.12 Bu/A. The gene candidate for editing is then ranked against other candidates based on that value. Edits may then be ranked in descending order of the products as disclosed above, resulting in some candidate edits ranking higher than other candidate edits. Expertise and previous experience with the genome editing engine 106, published literature and genome annotation, QTL studies, expressions studies, association tests, and/or use of machine learning may contribute to estimating the value of the probability/magnitude for each of the candidate edit. It should be understood that if those skilled in the art are concerned with altering multiple traits of the target organism (as compared a single trait of interest, for example, as defined at the outset of method 300 (i.e., grain yield)), overall ranking of candidate edits, by the genome editing engine 106, may be included in method 300, at 306, for example, in one or more ways. For example, the genome editing engine 106 may build an index across all or some of the multiple traits, for example, by a linear combination of several traits, and then the index may then become the frame of reference for ranking and evaluating the candidate edits.

Further, in some embodiments, ranking of the candidate edits may be accomplished by order of importance of the traits potentially impacted by the candidate edits, based on a determination for all candidate edits identified for that trait of interest causing the ranking of certain candidate edits to take precedence over candidate edits for other traits of interest as long as the calculated product based on the probability and/or magnitude is above a defined threshold. In the maize grain yield example, once the list of genes containing premature stop codons have been identified, the result of a QTL study may be used by the genome editing engine 106 or one or more persons to identify those located within QTL regions found in a yield mapping study. Redundant edits and edits to the genome sequence in non-QTL regions could be removed from the list of candidate edits, and unique edits to genes in QTL regions could then be ranked according to an estimated phenotypic effect. In such an approach, an assumption of the model may include that editing genes within the least favorable alleles at the QTL, will enhance the breeding value of those alleles in relation to more favorable alleles at the QTL.

In the 481 premature stop codons example described above, the genome editing engine 106 ranks the 481 stop codons in order based on the hybrid grain yield.

Next in FIG. 3, based on the ranking of the candidate edits, the genome editing engine 106 selects, at 308, multiple of the candidate edits from the population based on the ranking. Such selection may include selecting a specific number of candidate edits that may be technically combined, such as, for example, a maximum number of candidate edits, etc. The maximum number of edits would be limited by the technological capacity of performing a certain number of edits in the same plant (broadly, organism) at a feasible cost or within some restricted timeline, as inherent in and/or defined by the genome editing scheme 102. If few candidate edits are found and the population of selected candidate edits is smaller than the technological capability, then no further ranking would be needed. If multiple traits or candidate edits are being considered, an index combining all traits can be used for further ranking and selection. Alternatively, an optimization approach can be used to allocate a certain number of candidate edits to each trait until the maximum total permissible number is reached.

Referring again to the 481 premature stop codons example above, at steps 306 and 308, the genome editing engine 106 selects multiple genes based on ranking (and other suitable factors) (e.g., a top 10% in terms of the magnitude of their estimated yield impact, etc.), which includes, among others: GRMZM2G052586, GRMZM2G408775, GRMZM2G174687, and GRMZM2G367094. The selected premature stop codon alleles are predicted to have the following impact on grain yield, respectively: −1.05, −1.17, −1.67, and −1.25 Bu/A.

Then, once the candidate edits are selected, the genome editing engine 106 predicts, at 310, an aggregate effect of the selected multiple candidate edits to the genome sequence on at least one trait. Here, for example, the genome editing engine 106 predicts the grain yield of the maize inbred plant, based on identification of one or more disrupted genes within QTL regions. More generally, the aggregate effect of the selected candidate edits in the maize yield example is predicted, by the genome editing engine 106, based on an additive model. The additive model is based on a sum of the predicted effects of each edit within the selected candidate edits, per type, based on existing information or hypotheses about the edits (e.g., using high resolution genomic breeding values, bioinformatics based genome prediction, expression quantitative loci (e-QTL), historical performance of like-edits, etc.).

In one exemplary embodiment, the aggregate effect may be predicted, by the genome editing engine 106, by adding the predicted QTL effects of all QTL regions, in which one of the candidate edit was found. This aggregate effect assumes that, in each QTL region, the identified edit substantially explains the QTL effects. In numerous embodiments, the above aggregate effect determination may not be accurate, as a given candidate edit may only partially explain, or not at all explain, the observed and/or co-located QTL effect. In such embodiments, a correction factor may be used by the genome editing engine 106 to modify the aggregate effect prediction, thus deriving a risk adjusted aggregate effect prediction. This correction factor (e.g., scaled from 0 to 1, etc.) may then depend on the trait(s) of interest and/or the species of the target organism, as well as the experience accumulated at performing this process (e.g., observations from similar experiments to define/redefine the correction factor, etc.). For example, it may have been learned from previous experience that restoring functionality by repairing premature stop codons at all genes within a yield QTL region result in an average increase in yield that is about half or about 80% or some other suitable correction of the estimated effect between least and most favorable allele at the QTL. Thus, a correction factor of about 0.5 or about 0.8, for example, can then applied to models that predict the outcome of performing such tasks across novel yield QTLs and that use the sum of QTL effects as a predictor of the aggregate effect of the edits.

It should be appreciated that while an additive model is used herein, other models and/or non-additive models could also be built to account for possible dominance or epistatic interactions, and other models and/or non-parametric models could be used when selecting candidate edits with effects of unpredictable magnitude in other embodiments. An epi-static model may be applied when editing multiple genes in a biochemical pathway. If two genes in a pathway are non-functional, editing only one of those will not restore that pathway, but editing both will. Conversely, if an undesired phenotype is reached through multiple pathways, disrupting only one of these pathways may not change the phenotype, while disrupting all will. A non-parametric model could use heuristics to rank candidate edits, for example prioritize editing genes that are not member of multi-gene families or genes that are expressed in certain tissue types. Similarly, ranking candidate edits may be based on the evolutionary conservation of the gene to which the edits belongs, and prioritize editing genes which are modified and/or disrupted in a particular genome, but which have accumulated minimal, or little, genome sequence change within the species of interest or among other more distantly related species.

Referring again to the 481 premature stop codons example above, the genome editing engine 106 is able to predict the aggregate effect of the editing of the above four, listed premature stop codons is −5.14 Bu/A. Consequently, if all four were edited to wild-type full length alleles, it is predicted a yield increase of 5.14 Bu/A. When a correction factor, as described above, of about 80% is applied, for example, the predicted aggregate yield increase in this example becomes approximately 4 Bu/A (i.e., 4.1 Bu/A).

With continued reference to FIG. 3, the genome editing engine 106 then compares the predicted aggregate effect to one or more defined thresholds (e.g., maize yield is predicted to be increased by some amount over an unedited organism, etc.), at 312. The one or more defined threshold is determined, for example, by a minimum economic value required (or desired) for the predicted aggregate effect and/or the minimum improvement needed for statistical detection under a predetermined experimental validation protocol. With reference to the above 481 premature stop condos example, the genome editing engine 106 compares the 5.14 Bu/A to a threshold of 4 Bu/A, for example (as defined by the power calculation (step 312 of FIG. 3), whereby the predicted aggregate effect is above the threshold.

When the aggregate effect satisfies the defined threshold, the selected candidate edits corresponding to the aggregate effect are advanced into a validation phase of the method 300. If the predicted aggregate effect of all edits is below a practical detection threshold and/or below an economic threshold that justifies performing the candidate edits in vivo, then either one or more new approaches to identifying candidate edits may be pursued or, alternatively, the method 300 may be discontinued altogether. However, if the predicted aggregate effect reaches a commercially (or economical) viable threshold and/or experimentally testable (or practically detectable) threshold, the method 300 should be continued to validate the multiple selected candidate edits. For example, consider that the confirmation of the effectiveness of edits aimed at improving maize grain yield is conducted through the measurement of their aggregate effects in replicated yield trials. Assume a plot variance of 270 $Bu^2/A^2$, which is typical in a suitable central region of the United States (e.g., the Central Corn Belt, etc.) with 15 to 20 feet long plots with two rows 30 inches apart. If it is reasonable to replicate treatment (e.g., a line with an edited genome) and control (e.g., the same line without the edited genome) 265 times and desire a statistical power of 80%, that is an 80% probability of rejecting the null hypothesis when it is false, then an aggregate effect of 4 bushels/acre may be established as the defined threshold. Further details about such power calculations are provided below. Of course, one or more defined thresholds may be readjusted or defined otherwise, for example, as editing technologies improve (e.g., a maximum number of edits increases, etc.), cost associated with in vivo edits decreases, and/or prediction methodologies are refined (e.g., correction factors approaching one, etc.), where more precision may be achieved in measuring the difference between edited and unedited organism through one or more testing procedures, etc.

In the validation phase of the method 300, the genome editing engine 106 determines, at 314, the sample size to be used in validating the selected candidate edits.

Specifically, for example, in this exemplary embodiment, the genome editing engine 106 relies on a power consideration in determining the sample size for validation, 314. Assume that individual edits' effect, $\tau_i$, are additive, that is, the aggregate effect is the sum of the n individual effects. Further assume that measurement error at the individual plot level is normally distributed with mean 0 and variance $\sigma_e^2$. Then the difference between the mean performance across r replications of edited and control version, $\bar{x}_1$ and $\bar{x}_0$, respectively, is distributed normally according to Equation (1).

$$\bar{x}_1 - \bar{x}_0 \sim N(d = \Sigma_{i=1}^n \tau_i, 2\sigma_e^2/r) \quad (1)$$

With that said, the success of the genome editing engine 106 can be tested under the NULL hypothesis, $H_0$: $\bar{x}_1 - \bar{x}_0 \sim N(0, 2\pi_e^2/r)$. The power (P), or probability of rejecting $H_0$ when $H_0$ is false, under the alternative hypothesis $H_1$: $\bar{x}_1 - \bar{x}_0 \sim N(d, 2\sigma_e^2/r)$, can be determined through Equation (2). In Equation (2), $\beta$ represents a type II error (or failing to accept the alternative hypothesis when true) and d the effect size.

$$\text{Power} = P(1-\beta) = P(d - z_{1-\beta}\sqrt{2\sigma_e^2/r}) \quad (2)$$

Where $z_{1-\beta}$ is the value taken by Z, where $Z \sim N(d, 1)$, for which $P(Z < z_{1-\beta}) = 1 - \beta$ under the alternative hypothesis.

Therefore, to achieve the same power, the number of replicates required to validate the selected candidate edits is proportional to the error variance of the experimental units or inversely proportional to the square of the difference one is trying to detect. That is, if the error variance is reduced by half, only half as many replicates are needed. But to detect a difference in a given trait a tenth of the magnitude of the unedited organism, one hundred times as many replicates would be necessary to demonstrate that the difference is real. In the above example, an experiment unit or plot for the maize inbred includes 2 rows, 30 inches apart and 20 feet long, the number of maize plants in a plot would vary depending on density (e.g., where the density is generally between 38 and 36 thousand plants per acre, etc.). In an animal example, the experimental unit may include a single animal (e.g., a cow, etc.) or a cage, or pen with multiple animals (e.g., 5 egg-laying hens, etc.).

For illustration, in the example above, a validation methodology may identify candidate edits with an average effect on maize hybrid yield of 0.2 bushels (Bu) per acre (A), an edit-to-edit variance of 0.05 $Bu^2/A^2$, and a yield trial plot variance of 270 $Bu^2/A^2$ (which is typical in the Central Corn Belt, with 15 to 20 foot long plots and with two rows spaced 30 inches apart). If a particular edit had the effect of 0.2 Bu/A and the type I error is set at 5%, the total number of replicates across edited and control organisms needed to reject $H_0$ with a probability of 80%, pursuant to Equation (2) above, and conventional methods, would be approximately 212,000 replicates (106,000 for each edited and non-edited organism). As can be appreciated, this size may be unsuitable and/or impractical for implementation. As such, if a target organism (i.e., defining the genome sequence from step 302) could be modified with 20 edits with a combined predicted effect of 4 Bu/A (i.e., 20 times larger than the above example), only 265 replicate organism (which is approximately 400 times fewer replicate organisms (with respect to the 106,000)), for a total of 530 plots, thereby greatly reducing the resources required to obtain a power of 80%.

For illustration, in the above 481 premature stop codons example, if a power of 0.8 is assumed and a plot level variance of 270 Nu/A (and by use of Equation (2)), the genome editing engine 106 is able to estimate that 265 replicates are all that is required, necessary or desired, for validation of the predicted aggregate effect of the four selected genome edits.

Further, even if that particular selected candidate edit resulted in a combined effect which would fall in the 10% of combined effect size when producing 20 edits for that particular methodology, for which each effect is sampled from a normal distribution of mean 0.2 Bu/A and variance 0.05 $Bu^2/A^2$, this would provide, by the above, a combined effect of 2.71 Bu/A. As such, the number of replicate plots to be used to reject $H_0$ with a probability of 80% would be 578 each for the edited and unedited organism, totaling 1,156 plots, which is far fewer than the 212,000 plots described above. It should also be appreciated that if individual edits need to be ascertained with a methodology like above (mean 0.2 Bu/A, variance 0.05 $Bu^2/A^2$), there is a greater than 18% probability that any particular edit will have a negative impact (e.g., a reduced yield rather than an enhanced yield or an increased susceptibility to disease rate rather an reduce susceptibility to disease). That is, the actual effect is in the opposite direction of the predicted effect, with an edit resulting in a decrease in grain yield. This can be contrasted to the 0.003% probability that 20 such edits combined will have a negative aggregate effect.

In addition, the method 300, as described herein, permits multiple simultaneous edits to identify rare large effect edits. For example, assuming that 125 candidate edits are identified and/or exist, and only one has a very large effect, rather than testing each one of the edits separately, the edits may be tested together in 15 different combinations of 25 edits. As such, a 3-D pool concept may arise from the possibility of giving to each candidate edit a "row", "column", and "plate" number. In particular, the 125 candidate edits can be positioned in a 5×5×5 cubic data structure, where Variant 001 would be (1, 1, 1), while Variant 125 would be (5, 5, 5). The 15 pools (of 25 edits each) would be:

(1,-,-);(2,-,-);(3,-,-);(4,-,-);(5,-,-);(-,1,-);(-,2,-);(-,3,-);(-,4,-);(-,5,-);(-,-,1);(-,-,2);(-,-,3);(-,-,4);(-,-,5)

In connection therewith, if it is assumed, for example, that variant or block 52, which would be in position (3,1,2) in the exemplary cube, is the target, then three pools in which it will be found are (3,-,-), (-,1,-), and (-,-,2). The aggregate effect of lines edited with these three pools will have a larger effect than lines edited with the other 12 pools. Once again the number of replicate organisms, as described above, can be defined after a power calculation consistent with error variance and the size of the effect desired to be detected. Further, an amount of resources available to validate and/or measure the aggregate effect is constant. The genome editing engine 106 utilizing the above described pooling (as part of determining a sample size for validation) permits increasing the number of replicates per pool, as compared to testing each edit separately, thus increasing the power of the test and/or permitting detection of smaller effects with the same power.

Once the sample size is determined, a target organism (e.g., a maize plant), or set thereof, is/are modified, at 316, as defined in the selected multiple candidate edits. Specifically, the genome editing engine 106 provides not only the selected candidate edits to the genome editing scheme 102, as shown in FIG. 1, but also the sample size desired for validation, as determined above. Once the organism is modified, the organism is then passed to the cultivation space 104, as shown in FIG. 1, whereupon the organism is grown, cultivated, and/or cultured. At some later time, the aggregate effect of the selected candidate edits is measured in the organism, at 318. Thereafter, based on the measurements, an agronomic, economic, and/or scientific effect of the modified target organism is confirmed, at 320. To do so, for example, a difference between a mean performance for the trait of interest of edited and non-edited plants will provide an estimate of the realized aggregate effect. The number of replicates and measured error variance will help conduct a statistical test to accept or reject the null hypothesis (i.e., a null aggregate effect). The experimental results may also provide a confidence interval around the estimated realized aggregate effect. One skilled in the art will recognize that it may be more desirable to procure multiple edited plants for testing, and while this may necessitate more resources to estimate a realized aggregate effect in each edited plant, it may aid in confirming that measured differences are the result of the candidate edits being made to the organism, and not an uncontrolled change confounded with the edit in a single edited plant.

In view of the above, the systems and methods herein permit identification and selection of multiple candidate edits for validation, rather than singly investigating and validating individual edits one at a time, where the aggregate effect of the multiple candidate edits may be predicted. Stated another way, as described herein, measuring the aggregate effect of the multiple candidate edits is economically feasible, even when measuring each of the individual edit effect is not. Further, by judicious phenotyping of an aggregate effect across subset of potential edits, a cost-efficient way to identify the rare large-effect edits is provided. Also, the systems and methods herein permit identification of parallel genome editing as a way to improve one or more polygenic traits where changes to a single gene cannot be measured due to a relatively minimal, minor, or small effect the single change has on the trait, but where the corresponding aggregate effect of multiple edits is observable within an acceptably sized cultivation space and/or experiment. In addition, pooling of the candidate edits may be employed, whereby a subset of candidate edit can be used to identify the rare large effect edits within the pool which also includes numerous small to neutral effect edits. Finally, the systems and methods herein may provide one or more breeder useful information about which gene, set of genes, and/or sequences to manipulate to achieve a desired trait change and/or improvement, by assessing the aggregate effect of various combinations of particular modifications to a gene, set of genes, and/or sequences on a given trait. The above is provided through a data set, which is small by comparison to a data set sufficient to gauge the individual effect of each of dozens of SNPs or sequences on a given phenotypic trait (whereby the size is potentially secondary to the difficulty and expense of compiling such a data set).

The functions described herein, in some embodiments, may be described in computer executable instructions stored on a computer readable media, and executable by one or more processors. The computer readable media is a non-transitory computer readable media. By way of example, and not limitation, such computer readable media can include RAM, ROM, EEPROM, CD-ROM or other optical disk storage, magnetic disk storage or other magnetic storage device, or any other medium that can be used to carry or store desired program code in the form of instructions or data structures and that can be accessed by a computer. Combinations of the above should also be included within the scope of computer-readable media It should also be appreciated that one or more aspects of the present disclosure transform a general-purpose computing device into a special-purpose computing device when configured to perform the functions, methods, and/or processes described herein.

As will be appreciated based on the foregoing specification, the above-described embodiments of the disclosure may be implemented using computer programming or engineering techniques including computer software, firmware, hardware or any combination or subset thereof, wherein the technical effect may be achieved by performing at least one of the following operations: (a) identifying a population of candidate edits to a genomic sequence of said organism based on at least one of genome annotation, genome-wide association study (GWAS) analysis, gene expression data, and a biochemical pathway model; (b) ranking, by a computing device, each of the candidate edits based on a predicted ability of each candidate edit to affect a trait of interest in said organism, the predicted ability based on at least one of a probability of causing an effect, a magnitude of the effect, and a non-parametric classification parameter; (c) selecting, by the computing device, one or more of the candidate edits based on the ranking; and (d) predicting, by the computing device, an aggregate effect of the selected one or more of the candidate edits for the trait of interest when expressed by a specimen of the organism having a genomic sequence and edited according to the selected one or more of the candidate edits, as compared to an unedited specimen of the organism.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. In addition, advantages and improvements that may be achieved with one or more exemplary embodiments disclosed herein may provide all or none of the above mentioned advantages and improvements and still fall within the scope of the present disclosure.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises", "comprising", "including", and "having" are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When a feature is referred to as being "on", "engaged to", "connected to", "coupled to", "associated with", "in communication with", or "included with" another element or layer, it may be directly on, engaged, connected or coupled to, or associated or in communication or included with the other feature, or intervening features may be present. As used herein, the term "and/or" includes any and all combinations of one or more of the associated listed items.

Although the terms first, second, third, etc. may be used herein to describe various features, these features should not be limited by these terms. These terms may be only used to distinguish one feature from another. Terms such as "first", "second", and other numerical terms when used herein do not imply a sequence or order unless clearly indicated by the context. Thus, a first feature discussed herein could be termed a second feature without departing from the teachings of the example embodiments.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

Specific values disclosed herein are example in nature and do not limit the scope of the present disclosure. The disclosure herein of particular values and particular ranges of values for given parameters are not exclusive of other values and ranges of values that may be useful in one or more of the examples disclosed herein. Moreover, it is envisioned that any two particular values for a specific parameter stated herein may define the endpoints of a range of values that may be suitable for the given parameter (i.e., the disclosure of a first value and a second value for a given parameter can be interpreted as disclosing that any value between the first and second values could also be employed for the given parameter). For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9, and so forth.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for predicting a phenotypic impact of multiple genome edits in an organism, the method comprising:
identifying a population of candidate edits to a genomic sequence of said organism based on at least one of genome annotation, genome-wide association study (GWAS) analysis, gene expression data, and a biochemical pathway model;
ranking, by a computing device, each of the candidate edits based on a predicted ability of each candidate edit to affect one or more traits of interest in said organism, the predicted ability based on at least one of a probability of causing an effect, a magnitude of the effect, and a non-parametric classification parameter;
selecting, by the computing device, at least four of the candidate edits based on the ranking;
based on an additive model of predicted effects of the selected at least four of the candidate edits, per type, predicting, by the computing device, an aggregate effect of the selected at least four of the candidate edits for the one or more traits of interest expressed by a specimen of the organism having a genomic sequence and edited according to the selected at least four of the candidate edits, as compared to an unedited specimen of the organism;
determining, by the computing device, a sample size of replicates of the organism to be modified consistent with the selected at least four of the candidate edits for the one or more traits, based on the predicted aggregate effect and a defined probability threshold; and
modifying a number of the replicates of the organism, consistent with the sample size, according to the selected at least four of the candidate edits.

2. The method of claim 1, further comprising measuring an aggregate effect of the selected at least four of the candidate edits on the one or more traits of interest, based on the modified replicates of the organism and at least one un-modified replicate of the organism, thereby indicating the aggregate effect of the selected at least four of the candidate edits without measuring an effect of each of the selected at least four of the candidate edits individually.

3. The method of claim 1, further comprising subjecting the modified replicates of the organism to a cultivation space, whereby the aggregate effect is permitted to be verified.

4. The method of claim 3, wherein the organism includes a plant; and
wherein the one or more traits of interest is associated with economic importance.

5. The method of claim 4, wherein the organism includes a maize plant.

6. A method for generating a plant organism with an enhanced trait or phenotype, the method comprising:
identifying a population of candidate edits to a genomic sequence based on at least one of genome annotation, genome-wide association study (GWAS) analysis, gene expression data, and a biochemical pathway model;
ranking, by a computing device, each of the candidate edits based on a predicted ability of each candidate edit to affect a trait of interest, the predicted ability based on at least one of a probability of causing an effect, a magnitude of the effect, and a non-parametric classification parameter;
selecting, by the computing device, multiple ones of the candidate edits based on the ranking;
based on an additive model of predicted effects of the selected multiple ones of the candidate edits, per type, predicting, by the computing device, an aggregate effect of the selected multiple ones of the candidate edits for the trait of interest expressed by a specimen of a plant organism having a genomic sequence and edited according to the selected one or more of the candidate edits, as compared to an unedited specimen having the genomic sequence;

determining, by the computing device, a sample size of replicates of the specimen to be modified consistent with the selected multiple ones of the candidate edits for the trait of interest, based on the predicted aggregate effect and a defined probability threshold;

modifying a number of the replicates of the specimen, consistent with the sample size, according to the selected multiple ones of the candidate edits; and growing and/or cultivating said modified replicates in a cultivation space, along with an unedited plant organism consistent with the genomic sequence, thereby permitting validation of the predicted aggregate effect.

7. The method of claim 6, wherein the plant organism includes a maize plant.

8. The method of claim 6, wherein identifying the population of candidate edits includes identifying, by the computing device, the population of candidate edits; and wherein the method further comprises:

prior to modifying an unedited plant organism, determining a sample size to be used in invalidating the aggregate effect; and wherein modifying the unedited plant organism includes modifying multiple unedited plant organisms, consistent with the determined sample size, with the selected candidate edits.

9. A method of creating an agronomically advanced plant, the method comprising:

identifying a genomic sequence for a genome or pan-genome, identifying a population of candidate edits to the genomic sequence according to prior information including genome annotation, GWAS analyses, gene expression data, or biochemical pathway models;

rating, by a computing device, each of the candidate edits or groups of candidate edits in relation to a predicted ability to affect one or more phenotypes of interest, based on probability of causing an effect, magnitude of the predicted ability to cause the effect, and/or non-parametric classification parameter;

selecting, by the computing device, based on the rating, a subset of edits;

based on an additive model of predicted effects of the selected multiple ones of the candidate edits, per type, predicting, by the computing device, the aggregate effects of the preferred edits on the one or more phenotypes expressed by a plant with its genome sequence edited as compared to its unedited version, where a phenotypic impact of each individual edit may be too small to be proven significantly different from zero or to be estimated precisely;

determining, by the computing device, a sample size of replicates of the plant to be modified consistent with the selected subset of edits for the one or more phenotypes, based on the predicted aggregate effects and a defined probability threshold; and modifying a number of the replicates of the plant, consistent with the sample size, according to the selected multiple ones of the candidate edits.

10. The method of claim 9, wherein selection the subset of edits is further based on DNA fingerprints and/or pedigree relationships; and wherein the method further comprises:

measuring the aggregate effects of the edits by comparing the modified replicates of the plant to an unedited plant, the unedited plant having the same origin as the modified replicates of the plant; and confirming, based on the measured aggregate effect, the modified replicates of the plant, without individually measuring agronomic impact of each of the multiple edits.

* * * * *